US006861088B2

(12) United States Patent
Weber et al.

(10) Patent No.: US 6,861,088 B2
(45) **Date of Patent: *Mar. 1, 2005**

(54) METHOD FOR SPRAY-COATING A MEDICAL DEVICE HAVING A TUBULAR WALL SUCH AS A STENT

(75) Inventors: Jan Weber, Maple Grove, MN (US); Gordon John Kocur, Lino Lakes, MN (US)

(73) Assignee: Boston Scientific SciMed, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/809,765

(22) Filed: Mar. 24, 2004

(65) Prior Publication Data

US 2004/0185168 A1 Sep. 23, 2004

Related U.S. Application Data

(63) Continuation of application No. 10/109,073, filed on Mar. 28, 2002, now Pat. No. 6,743,463.

(51) Int. Cl.[7] ................................................ A16L 27/00

(52) U.S. Cl. ...................... 427/2.24; 427/2.1; 427/2.25; 427/2.28; 427/457; 427/458; 427/466; 427/471; 427/472; 427/476

(58) Field of Search ................................ 427/2.1, 2.24, 427/2.25, 2.28, 457, 458, 466, 472, 471, 476

(56) References Cited

U.S. PATENT DOCUMENTS

| | | | |
|---|---|---|---|
| 4,002,777 | A | 1/1977 | Juvinall et al. |
| 4,004,733 | A | 1/1977 | Law |
| 4,215,818 | A | 8/1980 | Hopkinson |
| 4,271,208 | A | 6/1981 | Itoh et al. |
| 4,341,347 | A | 7/1982 | DeVittorio |
| 4,376,143 | A | 3/1983 | Lehmann |
| 4,749,125 | A | 6/1988 | Escallon et al. |
| 6,355,058 | B1 | 3/2002 | Pacetti et al. |

*Primary Examiner*—Bret Chen
(74) *Attorney, Agent, or Firm*—Jones Day

(57) ABSTRACT

A method for electrostatic spray-coating a medical device having a tubular wall, such as a stent, having an inner surface, an outer surface and openings therein. The tubular wall is grounded or electrically charged, and an electrically charged conductive core wire is located axially through the center of the stent. An electrical potential is applied to the conductive core wire to impart an electrical charge to the conductive core wire. The tubular wall is exposed to an electrically charged coating formulation, and the electrically charged coating formulation is deposited onto a portion of the tubular wall to form a coating. The electrical potentials of the conductive core wire and tubular wall can be repeatedly alternated.

32 Claims, 4 Drawing Sheets

12
14
10
16

METHOD FOR SPRAY-COATING A MEDICAL DEVICE HAVING A TUBULAR WALL SUCH AS A STENT

This application is a continuation application of U.S. application Ser. No. 10/109,073, filed Mar. 28, 2002, now U.S. Pat. No. 6,743,463 and is incorporated herein by reference in its entirety.

FIELD OF THE INVENTION

The invention relates generally to a method for coating a stent or a medical device having a tubular wall. More particularly, the invention is directed to a method for electrostatic spray-coating a stent or a medical device having a tubular wall.

BACKGROUND OF THE INVENTION

Medical devices, such as implantable stents, have been coated with a coating comprising a biocompatible polymer to reduce adverse physiological reactions, such as restenosis, caused by uncoated surfaces of medical devices inserted or implanted in patient's body. Also, the coating can incorporate a biologically active material. For example, implanted stents have been used to carry medicinal agents, such as thrombolytic agents. See, U.S. Pat. No. 6,099,562 to Ding et al., U.S. Pat. No. 5,879,697 to Ding et al., Pinchuk to U.S. Pat. No. 5,092,877, U.S. Pat. No. 5,304,121 to Sahatjian.

Such coatings have been applied to the surface of a medical device by various methods, e.g., spray coating and dip coating. When a tubular wall, such as a stent, having openings therein is coated by conventional methods, it has been extremely difficult to coat only the inner surface of a tubular wall without coating the outer surface and vice versa. Also, the ratio of coating thickness placed on the inner surface of the tubular wall and placed on the outer surface of the tubular wall created by a conventional method is fixed and cannot be varied. For example, when a spray coating method is employed to coat such a tubular wall, the ratio of coating thickness depends on the configuration of the tubular wall, specifically, the size and shape of the openings therein. Accordingly, this ratio cannot be controlled. When a dip coating method is employed, the thickness of the coating on the inner surface and the outer surface is the same and cannot be varied. Also, conventional coating methods lack the ability to coat a tubular wall so that the coating thickness along the longitudinal axis of the tubular wall is varied.

Furthermore, in some medical devices having a tubular wall, all of the surfaces of the medical device or portions thereof may not need to be coated, or may not need to be coated with a coating comprising a biologically active material. For instance, the inner surface of a stent does not have to be coated with a coating containing a biologically active material when the biologically active material is intended to be delivered to a body lumen wall, which only directly contacts the outer surface of the stent. The inner surface of the stent does not come in direct contact with the body lumen wall and does not apply the biologically active material to the body lumen wall. On the other hand, if the biologically active material is intended to be delivered to a body fluid rather than a body lumen wall, then the coating containing the biologically active material should be placed on the inner surface of the stent wall but is not needed on the outer surface.

Also, in some instances, a release profile of a biologically active material can be optimized by varying coating thickness along longitudinal axis of the tubular wall. Specifically, in some stents, the amount of a coating containing a biologically active material may be preferably increased at the end sections of the tubular wall or stents as compared to the middle portion to reduce a risk of restenosis caused at the end sections.

In addition, coatings on different portions of the tubular wall may require different physical properties. For example, an expandable stent must be put in its unexpanded state or "crimped" before it is delivered to a body lumen. Thus, the coating on portions of the stent which contact each other in the stent's crimping state must not stick to each other and cause damage. In the case of a balloon expandable stent, the inner surface of the stent that contacts the balloon must not stick to the balloon during expansion. On the other hand, it is desirable to provide a relatively soft or "sticky" coating on the outer surface because it comes in direct contact with a body lumen wall.

Accordingly, there is a need for a method of coating a medical device comprising a tubular wall, such as a stent, that can control the thickness of coating on inner surface and outer surface. Furthermore, there is also a need for a method of coating a tubular wall, such as a stent, that can vary the thickness of coating along the longitudinal axis of the structure.

SUMMARY OF THE INVENTION

This and other objectives are accomplished by the present invention. To achieve these objectives, we have developed a method which is efficient to realize a controlled thickness of a coating on at least a portion of a medical device comprising a tubular wall, such as a stent, having an inner surface, an outer surface and openings therein. Specifically, in the method of the present invention, the tubular wall is grounded or electrically charged and a conductive core wire is located axially through the tubular wall. A potential is applied to the conductive core wire to impart an electrical charge to the conductive core wire. The tubular wall is exposed to an electrically charged coating formulation, and the charged coating formulation is deposited onto a portion of the tubular wall to form a coating on the tubular wall. In one embodiment, the tubular wall is grounded, and the conductive core wire and the coating formulation has the same electrical charge. In another embodiment, the tubular wall is grounded, and the conductive core wire and the coating formulation has opposite electrical charges. In yet another embodiment, the tubular wall and the coating formulation has the same electrical charge and the conductive core wire has an electrical charge opposite that of the tubular wall and the coating formulation. Alternatively, the potential applied to the conductive core wire may be pulsated to cyclically impart a positive electrical charge to the conductive core wire followed by a negative electrical charge.

In an embodiment, a core wire comprising a resistor material is located axially through the tubular wall instead of the conductive core wire, and a current is directed in the core wire. Two resistor wires may be located axially through the tubular wall.

Furthermore, in the method of the present invention, the core wire can be kept free of the coating formulation by, for example, using two bobbins, wherein one is feeding the core wire through the tubular wall and the other is winding the core wire. Also, in the method of the present invention, a pair of deflector plates can be used to direct the charged coating formulation.

DESCRIPTION OF THE PREFERRED EMBODIMENTS

In the method of the present invention, the amount of a coating formulation that is applied to a surface of a stent or tubular wall of a medical device is adjusted by employing the principles of electro-assisted spraying and a core wire located through the stent or tubular wall. The term "tubular wall" refers to a wall having a certain thickness configured in a shape of a tube or tubular structure. Such tubular structure may have a cross-section other than circle, such as an oval or square. In conventional electro-assisted spraying techniques, an electrically charged coating formulation is sprayed or applied to the surface of the device to be coated. The device is usually grounded or negatively charged. Since the coating formulation is a poor conductor, part of the electrical charge of the coating formulation is unable to escape. Therefore, those portions of the device surface that are coated with the coating formulation will have a higher potential than uncoated regions, and new particles or droplets of charged coating formulation applied to the device will be deflected to those uncoated regions of the device surface. In such method, the amount of coating formulation applied to the surface of the device tends to be uniformly spread over the entire surface. In contrast as explained further below, by locating an electrically charged core wire through the stent or tubular wall of the device, the amount of coating formulation applied on different surfaces or parts of a surface of the device can be varied.

In one embodiment of the present invention, the coating formulation is in a form of droplets. In other embodiments of the present invention, the coating formulation is in a form of dry or wet powder-particles.

Figure 1:
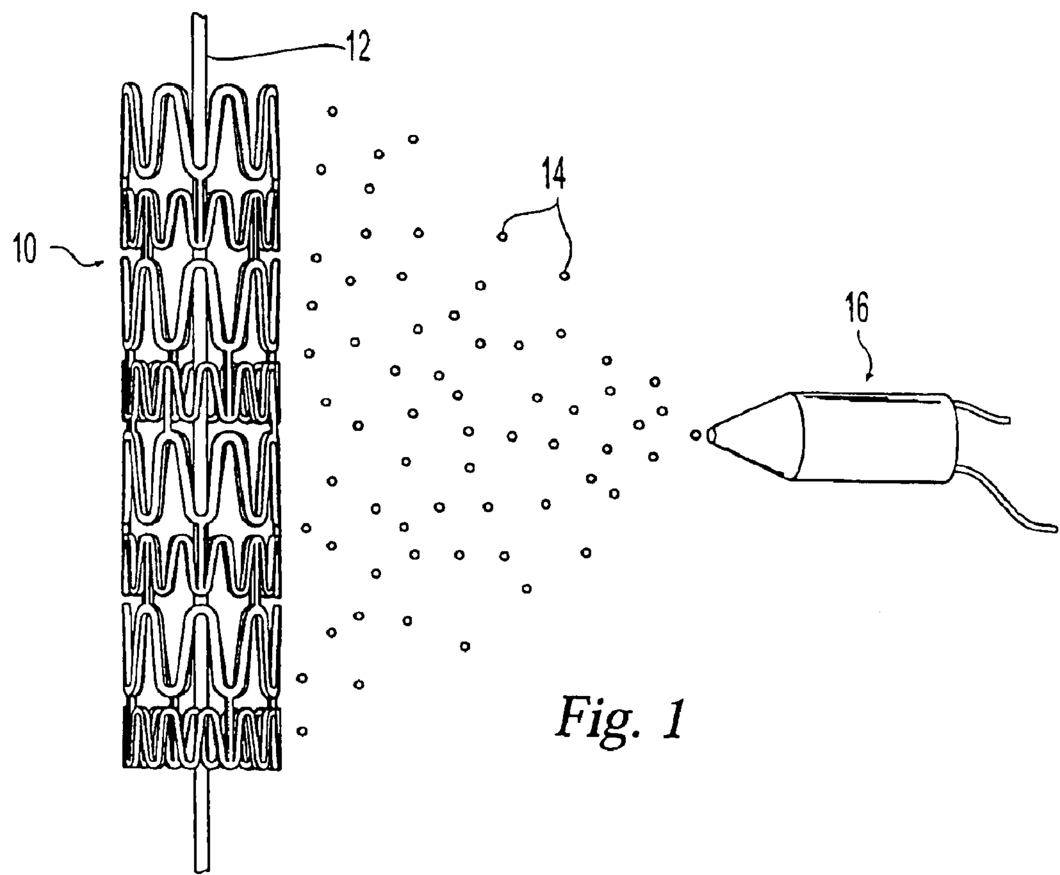
FIG. 1 depicts a perspective view of a spraying nozzle, particles or droplets of charged coating formulation, a stent and a core wire used in the method of the present invention.

Referring to FIG. 1, which depicts a perspective view of an arrangement for the method of the present invention wherein a conductive core wire 12 is located axially through a stent 10. Preferably, the core wire is located through the geometric center of the stent. A spray nozzle 16 is placed in proximity of the stent 10 and an electrically charged coating formulation 14 is sprayed to the stent 10.

Figure 2:
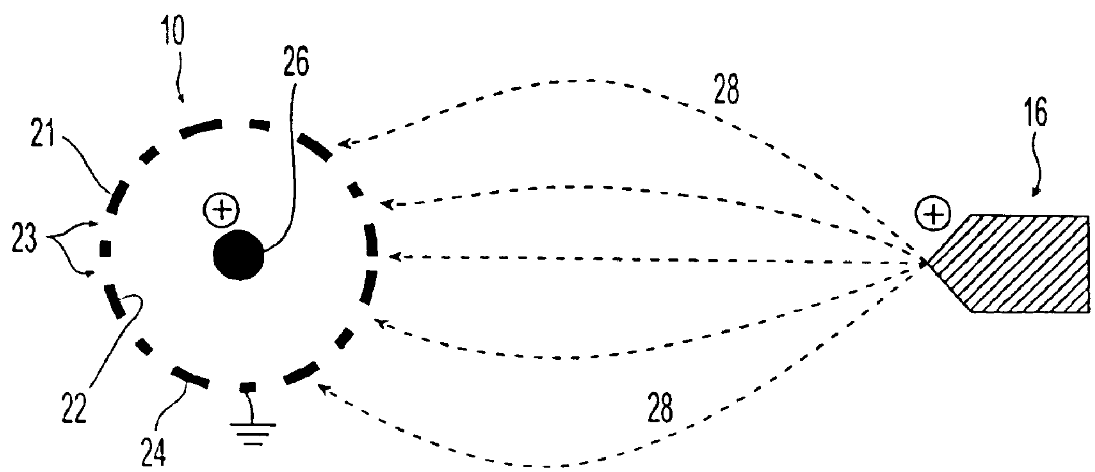
FIGS. 2–4 are illustrative cross-sectional views of a stent and a core wire along with a spray nozzle and representative routes of charged coating formulation in embodiments of the method of the present invention.

In an embodiment shown in FIG. 2, a stent 10 comprises a stent wall 21 having an inner surface 22, an outer surface 24 and openings therein 23. The stent wall 21 is grounded by a ground line so that it becomes electrically neutral. A potential is applied to a conductive core wire 26 located axially through the geometric center of the stent 10 to impart a positive electrical charge to the conductive core wire 26. The coating formulation is positively charged and sprayed from the nozzle 16 toward the stent 10. Because of its positive electrical charge, the sprayed coating formulation is attracted to the grounded stent 10 and is deposited on the outer surface 24 and side portions of the openings 23 of the stent wall 21. Representative routes of the sprayed charged coating formulation are shown as the arrows 28. The positively charged coating formulation does not enter the openings 23 due to the electrical repulsion of the positively charged core wire. Therefore, the electrically charged coating formulation is deposited only on the outer surface 24 and the side portions of the openings 23 of the stent wall 21, and the inner surface 22 of the stent wall 21 is maintained substantially free of coating.

Figure 3:
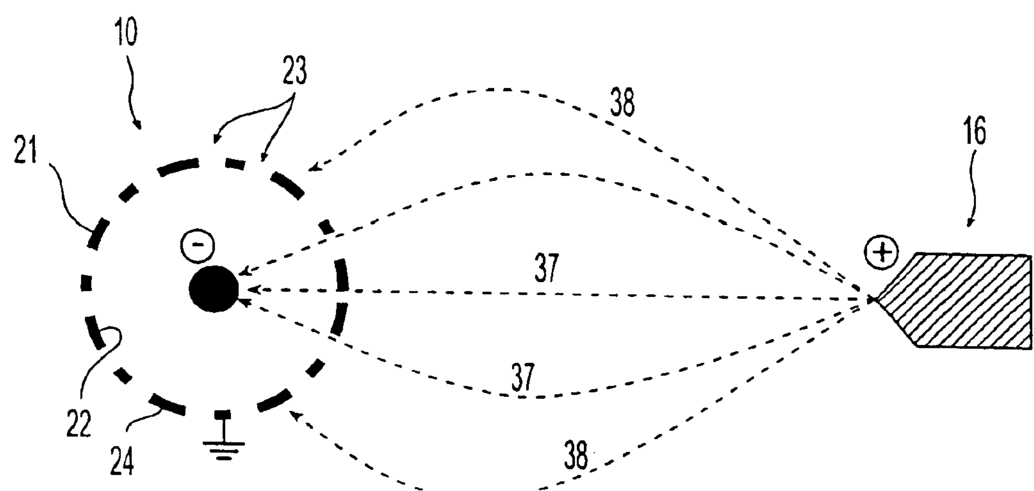

In an embodiment shown in FIG. 3, a stent 10 comprises a stent wall 21 having an inner surface 22, an outer surface 24 and openings therein 23. The stent wall 21 is grounded by a ground line so that it becomes electrically neutral. A conductive core wire 26 located axially through the geometric center of the stent 10 is negatively charged. The coating formulation is positively charged and sprayed from the nozzle 16 toward the stent 10. Because of its positive electrical charge, the sprayed coating formulation is attracted to the grounded stent wall 21. Some of the coating formulation is deposited on the outer surface 24 of the stent wall 21, and some of the coating formulation passes through the openings 23. Representative routes of the coating formulation are shown as the arrows 38. When the electrically charged coating formulation enters the openings 23, it is accelerated by virtue of the electrical forces of attraction and are attracted toward the conductive core wire 26. Therefore, the coating formulation is deposited only on the outer surface 24 of the stent wall 21, and the side portion of the openings 23 and the inner surface 22 of the stent are maintained substantially free of coating.

Figure 4:
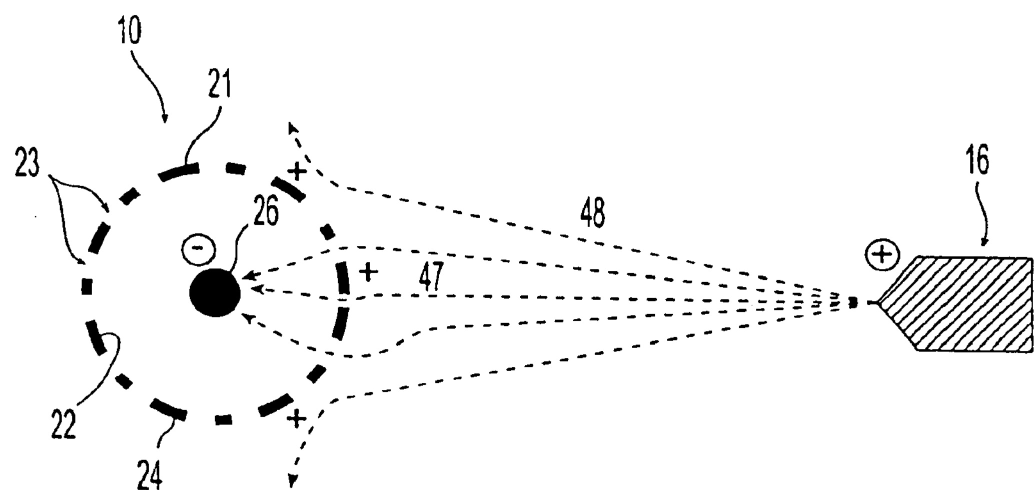

The embodiment shown in FIG. 4 is illustrative of how the method of the invention can be used to control how much coating is applied to the surface of a stent or a tubular wall. In this embodiment, a stent 10 comprises a stent wall 21 having an inner surface 22, an outer surface 24 and openings therein 23. The stent wall 21 is positively charged although its electrical potential is not high. A conductive core wire 26 located axially through the geometric center of the stent 10 is negatively charged. The coating formulation is positively charged and sprayed from the nozzle 16 toward the stent 10. Because of its positive electrical charge although the coating formulation is sprayed toward the stent 10, it is repelled by the positively charged stent 10. Representative routes of the coating formulation are shown as the arrows 48. When the coating formulation enters the opening 23, the coating formulation is attracted to the negatively charged conductive core wire 16 as shown by arrows 47. Therefore, the coating formulation is not deposited either on the inner surface 22 or on the outer surface 24 of the stent wall 21, and the stent is maintained substantially free of coating. This embodiment may be used to stop further coating formulation from being deposited, for example when a certain amount of coating has been reached. Also, this embodiment may be used to temporally stop coating the device for a period without stopping a continuous stable output from the nozzle.

Figure 5:
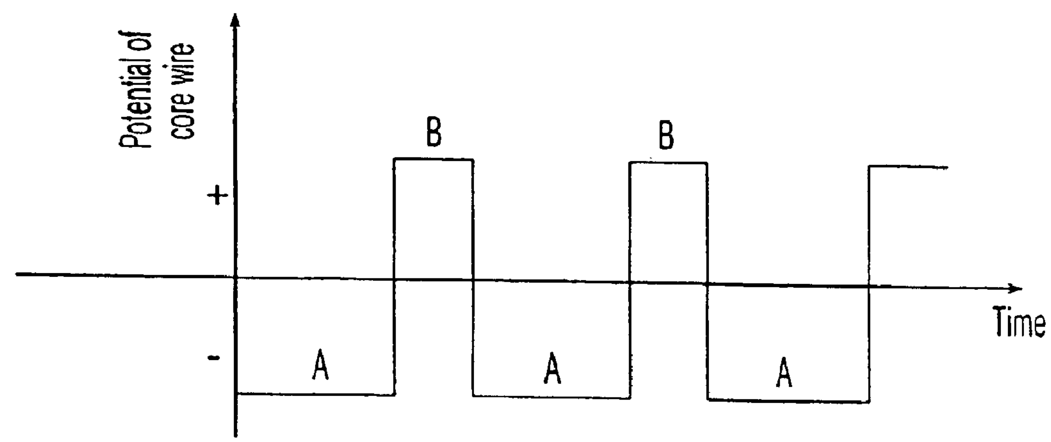
FIG. 5 is a graph showing a cyclic change of the electrical potential applied to the core wire in an embodiment of the method of the present invention.
Figure 6A:
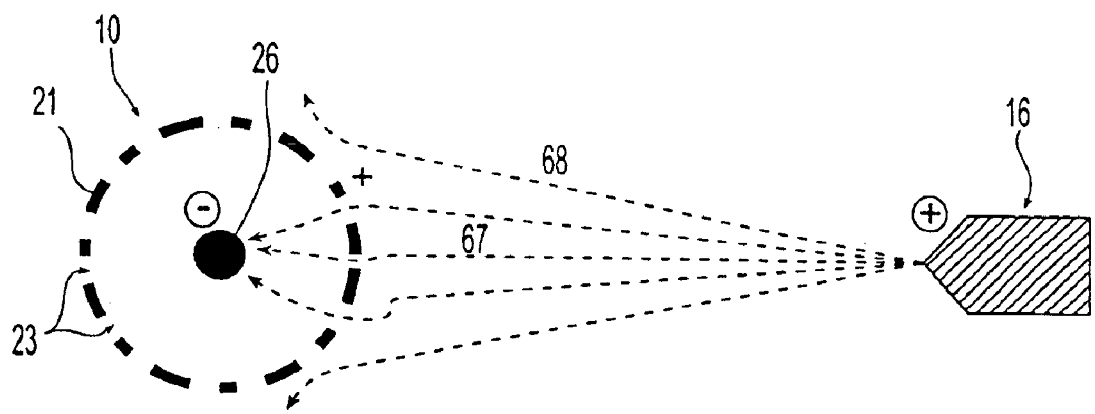
FIGS. 6A and 6B are illustrative cross-sectional views of a stent and a core wire along with a spray nozzle and representative routes of the charged coating formulation for two different states in the embodiment of the method of the present invention shown in FIG. 5.
Figure 6B:
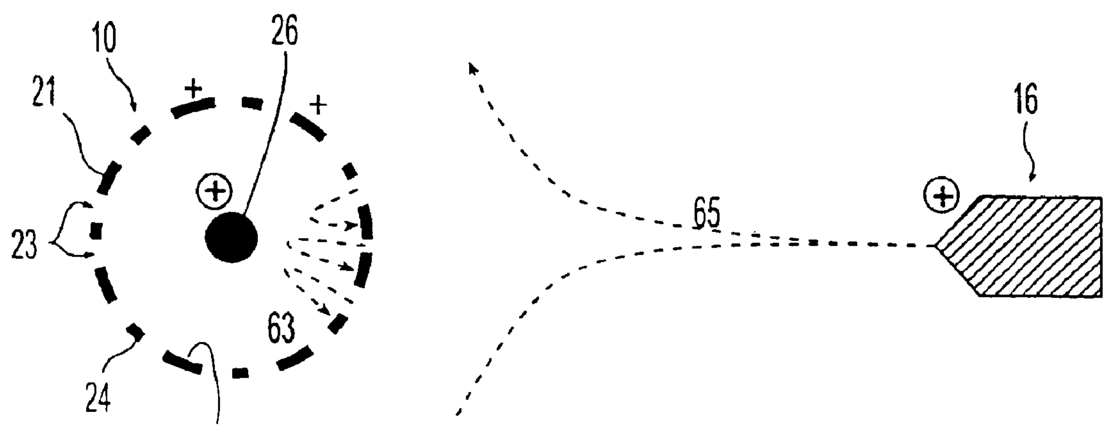

In an embodiment shown in FIGS. 6A and 6B, a stent 10 comprises a stent wall 21 having an inner surface 22, an outer surface 24 and openings therein 23. The stent wall 21 is positively charged although its electrical potential is not high. A conductive core wire 26 is located axially through the geometric center of the stent 10. The coating formulation is positively charged and sprayed from the nozzle 16 toward the stent 10. The electrical potential applied to the conductive core wire 26 is repeatedly alternatived between positive and negative as shown in the graph of FIG. 5. In FIG. 5, at first, the electrical potential of the conductive core wire is negative (State A) for a certain period, and changes to positive (State B), and again changes to negative (State A). States A and B are repeated in turn. FIG. 6A shows State A, wherein the stent wall 21 is positively charged (the electrical potential is not high), and the conductive core wire 26 is negatively charged. The coating formulation is positively charged and sprayed from the nozzle 16 toward the stent 10. Because of its positive electrical charge, although the coating formulation is sprayed toward the stent 10, majority of particles or droplets are repelled by the positively charged stent 10 as shown arrows 68. When particles or droplets of the coating formulation enter in the openings 23, the particles or droplets are attracted to the negatively charged conductive core wire 16 as shown by arrows 67. Therefore, the coating formulation are not deposited either on the inner surface 22 or on the outer surface 24 of the stent wall 21, and the stent is maintained substantially free of coating.

FIG. 6B shows State B, wherein the stent wall 21 is still positively charged as in State A, but the conductive core wire 26 is also positively charged. The electrical potential of the conductive core wire 26 is higher than that of the stent wall 21. The coating formulation is positively charged and sprayed from the nozzle 16 toward the stent 10. Because of its positive electrical charge, although the coating formulation is sprayed toward the stent 10, it is repelled by the positively charged stent 10 as shown by arrows 65. However, there is the coating formulation inside the stent 10 which was being attracted to but had not yet reached the then-negatively charged conductive core wire 26 in State A. The coating formulation inside the stent 10 is repelled by the core wire 26, which is now positively charged, and the coating formulation is deposited on the inner surface 22 of the stent wall 21 in State B. Therefore, in this embodiment, the coating formulation is deposited on the inner surface 22, and the outer surface 24 of the stent wall 21 is maintained substantially free of coating. Skilled artisans can optimize the electrical potentials (voltage) of the conductive core wire 26, the stent 10 and the coating formulation and the cycle (frequency) of the potential change to adjust the amount of coating applied to the inner surface 22 of the stent wall 21. Generally, the time period of State A is longer than that of State B. The period of State A is preferably long enough for sufficient amount of coating formulation to enter in the stent wall 21 through the openings 23 but shorter than necessary for the coating formulation to reach the conductive core wire 26. The period of State B is preferably not more than enough for substantially all coating formulation inside the stent wall 21 to be deposited on the inner surface 22 of the stent wall 21.

Each embodiment of the method of the present invention explained above can be conducted alone. The embodiment shown in FIG. 2 can be used to coat the outer surface and the side portions of the openings of a stent wall. The embodiment shown in FIG. 3 can be used to coat the outer surface of a stent wall. The embodiment shown in FIGS. 6A and 6B can be used to coat the inner surface of a stent wall.

Also, however, those embodiments may be combined, if desired. Particularly, the electrical potential applied to the stent wall may be repeatedly alternated between neutral and positive, and so may the electrical potential applied to the conductive core wire. By adjusting the frequency of the alternation and each electrical potential (voltage), it is possible to obtain any ratio of coating thickness on the inner surface, the outer surface and the side portions of the openings of the stent wall by using a continuous flow of sprayed coating formulation. For example, the following states may be employed to coat the device. Each state is part of a cycle, which can be repeated. During each of the states, the coating formulation remains positively charged:

| | |
|---|---|
| State A: | The stent wall has a positive electrical charge, but the potential applied to it is lower than that of the coating formulation. The conductive core wire has a negative electrical charge. (See FIG. 6A) |
| State B: | The stent wall has a positive electrical charge, and the conductive core wire has a positive electrical charge. The potential of the stent wall is lower than that of the coating formulation and the conductive core wire. (See FIG. 6B) |
| State C: | The stent wall is grounded, and the conductive core wire has a positive electrical charge. (See FIG. 2) |
| State D: | The stent wall is grounded, and the conductive core wire has a negative electrical charge. (See FIG. 3) |
| State E: | The stent wall has a positive electrical charge, but the potential applied to it is lower than that of the coating formulation. The conductive core wire has a negative electrical charge. (See FIG. 4) |

For example, arrangement of each electrical potential can be periodically switched starting from State A and changed to B, C, D, E and returning to A. During the period of States A–B, the coating formulation is deposited to the inner surface of the stent wall. During the period of State C, the coating formulation is deposited to the outer surface and side of the openings of the stent wall. Then, during the period of State D, the coating formulation is deposited to the outer surface of the stent wall, and during the period of State E, the coating formulation is not deposited to the stent wall. To increase the amount of coating placed on the inner surface, the length of time in States A+B should be increased. Likewise, to increase the amount of coating placed on the outer surface, the period of time in States C+D should be increased.

Moreover, the coating formulation may be negatively charged instead of being positively charged. If the coating formulation is negatively charged, then the stent is grounded or negatively charged, and the electrical potentials of the conductive core wire explained in the above embodiments are reversed.

Further, by adjusting time necessary for the coating formulation to reach to the surface to be coated in the above embodiments, it is possible to control the wetness of the coating formulation that arrive at a surface. The time can be adjusted by increasing or decreasing the field strength, specifically the electrical potentials of the coating formulation, the stent and the conductive core wire. If it takes longer for the coating formulation to get from the nozzle to the surface, then the coating formulation is dryer when it reaches the surface. If it takes less time for the coating formulation to get from nozzle to the surface, then the coating formulation is wetter when it reaches the surface. An appropriate wetness of the coating formulation must be chosen to obtain a coating layer which has desired physical properties and desired release profile of the biologically active material. For example, by choosing an appropriate wetness of the coating formulation in liquid form, it is possible to control the coating porosity. Such ability to control porosity is useful for preparing a coating for release a biologically active material.

In embodiments of the method of the present invention a stent can be coated with a multiple coating layers of the same coating formulation. Such coating layers may be made by using the above mentioned method repeatedly. The thickness of each coating layer curl be controlled as explained above. Also, the coating comprises various coating layers of different coating formulations. Such different coating layers can be efficiently made by using the present invention. For example, a first nozzle containing a first coating formulation may be first used to coat the outer surface of a stent by the above-mentioned embodiment of the method of the present invention, and then a second nozzle containing a second coating formulation may be used to coat the outer surface which is already coated with the first coating formulation. If desired, it is possible to coat a surface with the first coating formulation and coat the other surface with the second coating formulation which is different from the first coating formulation.

Figure 7:
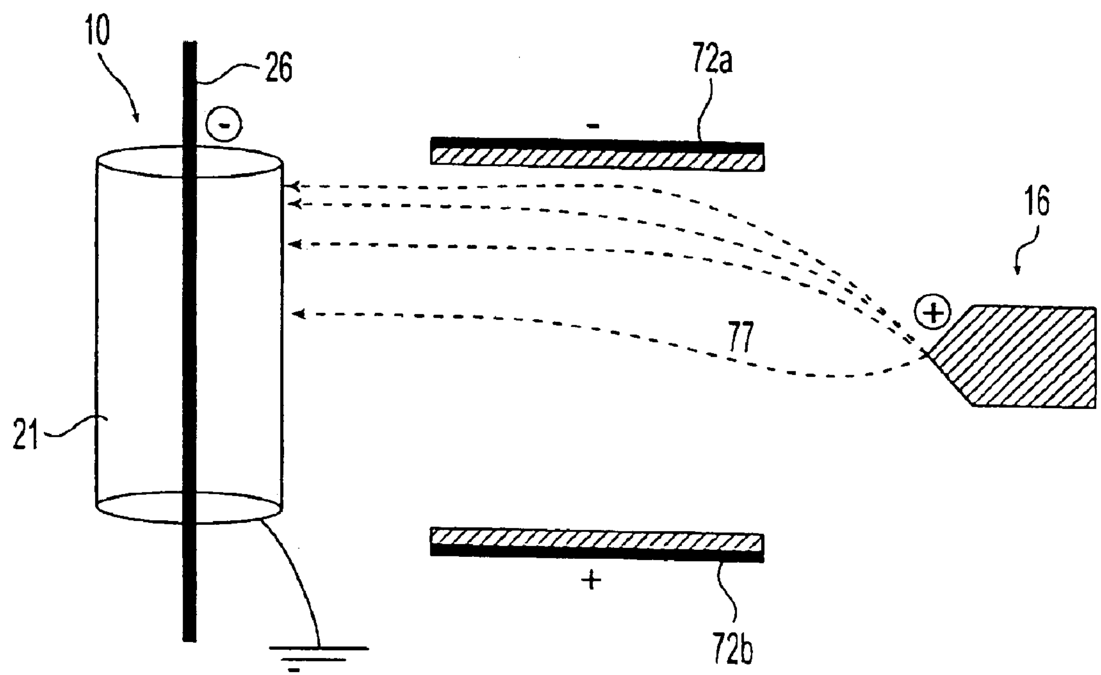
FIG. 7 is an illustrative view of a spraying nozzle, a stent, a core wire, a pair of deflector plates, and representative routes of sprayed charged coating formulation, that are arranged for another embodiment of the method of the present invention.

In addition to controlling the ratio of coating thickness on the inner surface, the outer surface and the side portions of the openings of the stent wall, the coating thickness along the longitudinal axis of a stent or a tubular wall can be controlled by an embodiment of the method of the present invention. Referring to FIG. 7, a pair of deflector plates 72*a* and 72*b* are added to an embodiment of the present invention shown in FIG. 3. The pair of deflector plates are a first deflector plate 72*a* having a negative electrical charge and a second deflector plate 72*b* having a positive electrical charge, which are parallel to each other. The pair of deflector plates 72*a*, 72*b* are placed parallel to the direction in which the coating formulation is sprayed from the nozzle 16 toward the stent 10. The positively charged coating formulation is attracted to the negatively charged deflector plate 72*a* and the course of the charged coating formulation is deflected toward the deflector plate 72*a* as shown by arrow 77. However, the electrical potential between the deflector plates 72*a* and 72*b* is so small that a majority of particles or droplets of the coating formulation do not contact the negatively charged deflector plate 72*a*. The distribution of the coating formulation on the stent wall 21 in its longitudinal direction can be controlled by using the deflector plates. For example, a stent having a coating which covers only one edge or end section of the stent can be obtained. If the potential is reversed, then the other edge or end section will also be covered by the coating, and a stent having a thicker coating at both end sections and thinner coating in the middle section can be obtained. The term "end section" of the outer surface refers to that part of the surface which extends from an end section or edge of a stent or a tubular wall up to about 25%, preferably from about 3% to about 20% of the entire length of the outer surface. The term "middle section" refers to the remainder of the outer surface that is surrounded by the end sections as defined above.

When the potential is reversed, the coating formulation may be switched from the first coating formulation to the second coating formulation so that a tubular wall can have a different type of coating on its end sections. By using different electrical potentials and varying the time such potentials are applied, sophisticated control of the coating can be achieved. For example, coating only a horizontal belt-like portion of the tubular wall or horizontal stripes of the tubular wall, is possible by adjusting the potential between the pair of deflector plates and adjusting the position of the deflector plates relative to the tubular wall.

Figure 8:
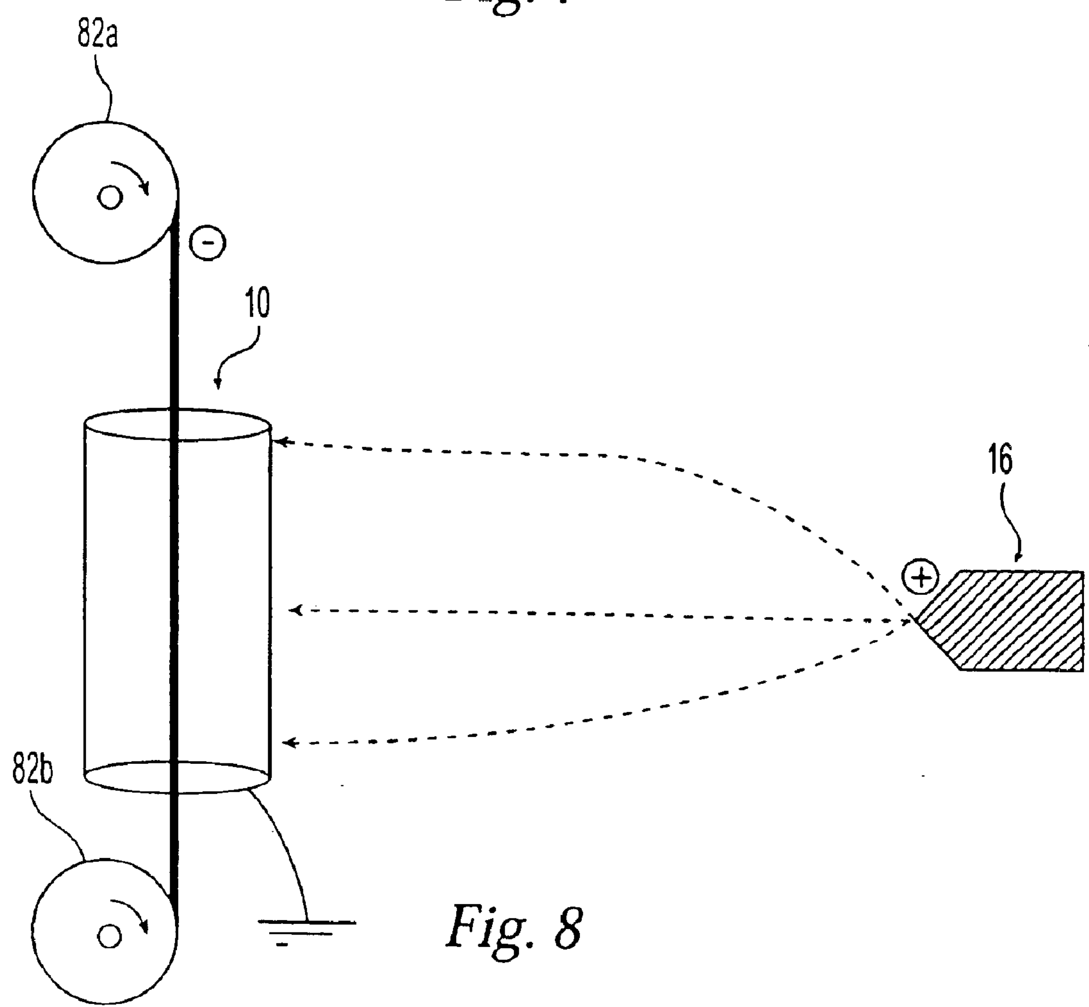
FIG. 8 is an illustrative view of a spraying nozzle, a stent, a core wire, a pair of bobbins, and representative routes of sprayed charged coating formulation in yet another embodiment of the method of the present invention.

When the electrical charge of the conductive core wire is opposite to that of the sprayed coating formulation, the coating formulation can be deposited on the conductive core wire in the method of the present invention. Since the coating formulation has poor conductivity, the electrical potential of the wire becomes weaker as more coating formulation accumulates on the wire. To prevent such weakening potential of the conductive core wire, the wire is preferably kept substantially free from the coating formulation. For example, a pair of bobbins can be used to feed new conductive core wire through a stent as shown in FIG. 8. A first bobbin 82*a* on which a substantial length of conductive core wire is wound is one side of the stent 10 and the conductive core wire 26 is passed axially through the stent 10 and the other end section of the conductive core wire 26 is connected to a second bobbin 82*b*. As a portion of the conductive core wire is constantly unwound from the first bobbin 82*a* and fed through the stent 10, the conductive core wire covered with the coating formulation is removed and connected to the second bobbin 82*b*.

In one embodiment of the method of the present invention, a core wire made of a resistor material is used instead of a conductive core wire, and a current is directed through the wire. Since the potential of the core wire comprised of a resistor material is a function of the longitudinal position along the core wire, more electrically charged coating formulation is deposited on the portion of the surface of the tubular wall that is closer to the part of the core wire having higher opposite potential to the charged coating formulation. If two parallel core wires of resistor material are provided in a stent wherein opposing currents are directed, a stent having thicker coating at both end sections and thinner coating in the middle section can be obtained. A pair of bobbins or a pair of deflector plates explained above can also be used for core wires made of a resistor material.

Although the above embodiments of the method of the present invention are explained using a stent as an example of a medical device having a tubular wall, the method of the present invention can be used generally for coating at least a portion of a surface of a medical device comprising a tubular wall having an inner surface and an outer surface and openings therein. A preferable medical device is designed to be inserted or implanted into the body of a patient. Such medical devices suitable for the present intention include, but are not limited to, stents, vascular or other grafts, and filters, such as blood filters.

Medical devices which are particularly suitable for the present invention include stents, for example, vascular stents such as self-expanding stents and balloon expandable stents. Stents suitable for the present invention include any stent for medical purposes, which are known to the skilled artisans. Particularly the method of the present invention is useful for coating stents having intricate surfaces. Examples of self-expanding stents useful in the present invention are illustrated in U.S. Pat. Nos. 4,655,771 and 4,954,126 issued to Wallsten and U.S. Pat. No. 5,061,275 issued to Wallsten et al. Examples of appropriate balloon-expandable stents are shown in U.S. Pat. No. 5,449,373 issued to Pinchasik et al.

The medical devices suitable for the present invention may be fabricated from conductive materials, such as conductive ceramic, polymeric and metallic materials. The surface(s) of the medical devices to be coated using the process of the present invention should be fabricated from conductive materials. Suitable metallic materials include metals and alloys based on titanium (such as nitinol, nickel titanium alloys, thermo-memory alloy materials), stainless steel, tantalum, nickel-chrome, or certain cobalt alloys including cobalt-chromium-nickel alloys such as Elgiloy® and Phynox®. Metallic materials also include clad composite filaments, such as those disclosed in WO 94/16646. An example of a suitable ceramic is carbide. Polymers can be used to fabricate the medical device when they are conductive. These include polymers filled with carbon-nanotubes. Carbon-nanotubes are commercially available, e.g., from CARBOLEX. Only the surface to be coated rather than entire medical device may be fabricated from a conductive material.

The core wire can be made of a conductive material. The surface of core wire should be conductive. Suitable conductive materials include those described materials for the medical device. In an embodiment of the method of the present invention, the core wire is made of a resistor material, such as carbon, a polymer filled with carbon nanotubes.

Any spraying nozzle or spraying device that can spray coating formulation and create particles or droplets of an appropriate size and of appropriate electrical charge is useful for the method of the present invention. Examples of such spraying nozzle are disclosed in U.S. Pat. No. 4,341,347 to DeVittorio, U.S. Pat. No. 4,004,733 to Law, U.S. Pat. No. 4,215,818 to Hopkinson, and U.S. Pat. No. 4,002,777 to Juvinall et al. One preferable example of a spraying nozzle that can be used in the method of the invention is an apparatus for electrohydrodynamic spray-coating that is disclosed in U.S. Pat. No. 4,749,125, to Escallon et al.

Coating formulations that are useful for the method of the present invention may be a solution or a suspension comprises a polymeric material and solvent or may be powder comprising a polymeric material. The polymeric material useful for forming the coating formulation should be ones that are biocompatible and avoids irritation to body tissue. Preferably the polymeric materials are biostable ones such as polyurethanes, silicones (e.g., polysiloxanes and substituted polysiloxanes), and polyesters. Also preferable as a polymeric material is styrene-isobutylene copolymers. Other polymers which can be used include ones that can be dissolved and cured or polymerized on the medical device or polymers having relatively low melting points that can be blended with biologically active materials. Additional suitable polymers include, thermoplastic elastomers in general, polyolefins, polyisobutylene, ethylene-alphaolefin copolymers, acrylic polymers and copolymers, vinyl halide polymers and copolymers such as polyvinyl chloride, polyvinyl ethers such as polyvinyl methyl ether, polyvinylidene halides such as polyvinylidene fluoride and polyvinylidene chloride, polyacrylonitrile, polyvinyl ketones, polyvinyl aromatics such as polystyrene, polyvinyl esters such as polyvinyl acetate, copolymers of vinyl monomers, copolymers of vinyl monomers and olefins such as ethylene-methyl methacrylate copolymers, acrylonitrile-styrene copolymers, ABS (acrylonitrile-butadiene-styrene) resins, ethylene-vinyl acetate copolymers, polyamides such as Nylon 66, Nylon 12 and polycaprolactone, alkyd resins, polycarbonates, polyoxymethylenes, polyimides, polyethers, epoxy resins, rayon-triacetate, cellulose, cellulose acetate, cellulose butyrate, cellulose acetate butyrate, cellophane, cellulose nitrate, cellulose propionate, cellulose ethers, carboxymethyl cellulose, collagens, chitins, polylactic acid, polyglycolic acid, polylactic acid-polyethylene oxide copolymers, EPDM (etylene-propylene-diene) rubbers, fluorosilicones, polyethylene glycol, polysaccharides, phospholipids, combinations of the foregoing.

More preferably for medical devices which undergo mechanical challenges, e.g. expansion and contraction, the polymeric materials should be selected from elastomeric polymers such as silicones (e.g. polysiloxanes and substituted polysiloxanes), polyurethanes, thermoplastic elastomers, ethylene vinyl acetate copolymers, polyolefin elastomers, and EPDM rubbers. Because of the elastic nature of these polymers, the coating adheres better to the surface of the medical device when the device is subjected to forces, stress or mechanical challenge.

Furthermore, although the invention can be practiced by using a single type of polymer to form the coating layer(s), various combinations of polymers can be employed. The appropriate mixture of polymers can be coordinated with biologically active materials of interest to produce desired effects when coated on a medical device in accordance with the invention.

Coating formulations useful for the present invention may contain a nanocomposite instead of or in addition to a polymeric material explained above. "Nanocomposite" is a term of art that refers to a composition comprising a polymeric material and relatively small amounts (generally less than about 10% by weight) of nanometer-sized (average size smaller than 1 micrometer) mineral clay or nanosized ceramic particles dispersed therein. Sometimes nanocomposites are referred to as "nanoclay" or "nanoceramic". For example, nanocomposites are disclosed in WO 931014118, U.S. Pat. Nos. 5,385,776, and 6,251,980.

Solvents suitable for forming the coating formulation are ones which can dissolve the polymeric material into solution or form dispersions of the polymeric material in the solvent. Any solvent which does not alter or adversely impact the therapeutic properties of the biologically active material can be employed in the method of the present invention. Examples of useful solvents include tetrahydrofuran, chloroform, toluene, acetone, isooctane, 1,1,1,-trichloroethane, and mixture thereof. Preferably, chloroform or tetrahydrofuran is used as the solvent in the method of the present invention.

Coating formulations useful for the present invention that are in powder form can comprise a polymeric material as explained above. The powder is preferably comprised of particles having an average diameter from about 0.5 μm to about 250 μm. Generally, the resulting surface of the coating is smoother when the powder of the coating formulation used for the coating has a smaller average particle size. After the spray-coating step using the powder coating formulation, the tubular wall coated with the powder coating formulation is heat-treated, for example using IR heating.

Even when the coating formulation used for the present invention contains a solvent, it is possible to control the process to dry the sprayed coating formulation before they reach the tubular wall of the medical device by controlling the method as explained earlier. In this manner, results similar to those of the process using dry-powder coating formulation can be obtained by using the coating formulation containing a solvent.

Coating formulations useful for the method of the present invention may also comprise a biologically active material. The term "biologically active material" encompasses therapeutic agents, such as drugs, and also genetic materials and biological materials. The genetic materials mean DNA or RNA, including, without limitation, of DNA/RNA encoding a useful protein stated below, anti-sense DNA/RNA, intended to be inserted into a human body including viral vectors and non-viral vectors. Examples of DNA suitable for the present invention include DNA encoding anti-sense RNA tRNA or rRNA to replace defective or deficient endogenous molecules angiogenic factors including growth factors, such as acidic and basic fibroblast growth factors, vascular endothelial growth factor, epidermal growth factor, transforming growth factor α and β, platelet-derived endothelial growth factor, platelet-derived growth factor, tumor necrosis factor α, hepatocyte growth factor and insulin like growth factor cell ccle inhibitors including CD inhibitors thymidine kinase ("TK") and other agents useful for interfering with cell proliferation, and the family of bone morphogenic proteins ("BMP's") as explained below. Viral vectors include adenoviruses, gutted adenoviruses, adeno-associated virus, retroviruses, alpha virus (Semliki Forest, Sindbis, etc.), lentiviruses, herpes simplex virus, ex vivo modified cells (e.g., stem cells, fibroblasts, myoblasts, satellite cells, pericytes, cardiomyocytes, sketetal myocytes, macrophage), replication competent viruses (e.g., ONYX-015), and hybrid vectors. Non-viral vectors include artificial chromosomes and mini-chromosomes, plasmid DNA vectors (e.g., pCOR), cationic polymers (e.g., polyethyleneimine, polyethyleneimine (PEI)) graft copolymers (e.g., polyether-PEI and polyethylene oxide-PEI), neutral polymers PVP, SP1017 (SUPRATEK), lipids or lipoplexes, nanoparticles and microparticles with and without targeting sequences such as the protein transduction domain (PTD).

The biological materials include cells, yeasts, bacteria, proteins, peptides, cytokines and hormones. Examples for peptides and proteins include growth factors (FGF, FGF-1, FGF-2, VEGF, Endotherial Mitogenic Growth Factors, and epidermal growth factors, transforming growth factor α and β, platelet derived endothelial growth factor, platelet derived growth factor, tumor necrosis factor α, hepatocyte growth factor and insulin like growth factor), transcription factors, proteinkinases, CD inhibitors, thymidine kinase, and bone morphogenic proteins (BMP's), such as BMP-2, BMP-3, BMP-4, BMP-5, BMP-6 (Vgr-1), BMP-7 (OP-1), BMP-8. BMP-9, BMP-10, BMP-11, BMP-12. BMP-13, BMP-14, BMP-15, and BMP-16. Currently preferred BMP's are BMP-2, BMP-3, BMP-4, BMP-5, BMP-6, BMP-7. Alternatively or in addition, molecules capable of inducing an upstream or downstream effect of a BMP can be provided. Such molecules include any of the "hedgehog" proteins, or the DNA's encoding them. These dimeric proteins can be provided as homodimers, heterodimers, or combinations thereof, alone or together with other molecules. Cells can be of human origin (autologous or allogeneic) or from an animal source (xenogeneic), genetically engineered, if desired, to deliver proteins of interest at the transplant site. The delivery media can he formulated as needed to maintain cell function and viability. Cells include whole bone marrow, bone marrow derived mono-nuclear cells, progenitor cells (e.g., endothelial progentitor cells) stem cells (e.g., mesenchymal, hematopoietic, neuronal), pluripotent stem cells, fibroblasts, macrophage, and satellite cells.

Biologically active material also includes non-genetic therapeutic agents, such as:

anti-thrombogenic agents such as heparin, heparin derivatives, urokinase, and PPack (dextrophenylalanine proline arginine chloromethylketone);

anti-proliferative agents such as enoxaprin, angiopeptin, or monoclonal antibodies capable of blocking smooth muscle cell proliferation, hirudin, and acetylsalicylic acid, amlodipine and doxazosin;

anti-inflammatory agents such as glucocorticoids, betamethasone, dexamethasone, prednisolone, corticosterone, budesonide, estrogen, sulfasalazine, and mesalamine;

immunosuppressants such as sirolimus (RAPAMYCIN), tacrolimus, everolimus and dexamethasone, antineoplastic/antiproliferative/anti-miotic agents such as paclitaxel, 5-fluorouracil, cisplatin, vinblastine, vincristine, epothilones, methotrexate, azathioprine, halofuginone, adriamycin, actinomycin and mutamycin; endostatin, angiostatin and thymidine kinase inhibitors, and its analogs or derivatives;

anesthetic agents such as lidocaine, bupivacaine, and ropivacaine;

anti-coagulants such as D-Phe-Pro-Arg chloromethyl keton, an RGD peptide-containing compound, heparin, antithrombin compounds, platelet receptor antagonists, antithrombin anticodies, anti-platelet receptor antibodies, aspirin (aspirin is also classified as an analgesic, antipyretic and anti-inflammatory drug), dipyridamole, protamine, hirudin, prostaglandin inhibitors, platelet inhibitors and tick antiplatelet peptides;

vascular cell growth promotors such as growth factors, Vascular Endothelial Growth Factors (FEGF, all types including VEGF-2), growth factor receptors, transcriptional activators, and translational promotors;

vascular cell growth inhibitors such as antiproliferative agents, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin;

cholesterol-lowering agents; vasodilating agents; and agents which interfere with endogenous vasoactive mechanisms;

anti-oxidants, such as probucol;

antibiotic agents, such as penicillin, cefoxitin, oxacillin, tobranycin angiogenic substances, such as acidic and basic fibrobrast growth factors, estrogen including estradiol (E2), estriol (E3) and 17-Beta Estradiol; and drugs for heart failure, such as digoxin, beta-blockers, angiotensin-converting enzyme (ACE) inhibitors including captopril and enalopril.

Also, the biologically active materials of the present invention include nitric oxide adducts, which prevent and/or treat adverse effects associated with use of a medical device in a patient, such as restenosis and damaged blood vessel surface. Typical nitric oxide adducts include nitroglycerin, sodium nitroprusside, S-nitroso-proteins, S-nitroso-thiols, long carbon-chain lipophilic S-nitrosothiols, S-nitrosodithiols, iron-nitrosyl compounds, thionitrates, thionitrites, sydnonimines, furoxans, organic nitrates, and nitrosated amino acids, preferably mono-or poly-nitrosylated proteins, particularly polynitrosated albumin or polymers or aggregates thereof. The albumin is preferably human or bovine, including humanized bovine serum albumin. Such nitric oxide adducts are disclosed in U.S. Pat. No. 6,087,479 to Stamler et al. which is incorporated herein by reference.

A biologically active material may be encapsulated in micro or nano-capsules by the known methods.

The biologically active material can be used with (a) biologically non-active material(s) including a carrier or an excipient, such as sucrose acetate isobutyrate (SABER™ commercially available from SBS) ethanol, n-methyl pymolidone, dimethyl sulfoxide, benzyl benxoate, benzyl acetate, albumine, carbohydrate, and polysacharide. Also, nanoparticles of the biologically active materials and non-active materials are useful for the coating formulation of the present invention.

The description contained herein is for purposes of illustration and not for purposes of limitation. Changes and modifications may be made to the embodiments of the description and still be within the scope of the invention. Furthermore, obvious changes modifications or variations will occur to those skilled in the art. Also, all references cited above are incorporated herein in their entirety, for all purposes related to this disclosure.

We claim:

1. A method for coating a medical device comprising a tubular wall having an inner surface, an outer surface and openings therein, wherein the method comprises:

(a) grounding or electrically charging the tubular wall;

(b) providing a conductive core wire located axially through the tubular wall;

(c) applying a potential to the conductive core wire to impart an electrical charge to the conductive core wire;

(d) exposing the tubular wall to an electrically charged coating formulation comprising a biologically active material; and (e) depositing the coating formulation onto a portion of the tubular wall to form a coating on the tubular wall.

2. The method of claim 1, wherein the biologically active material comprises an immunosuppressant, an antiproliferative agent, or a combination thereof.

3. The method of claim 2, wherein the immunosuppressant comprises sirolimus, everolimus, tacrolimus, or a combination thereof.

4. The method of claim 2, wherein the antiproliferative agent comprises paclitaxel, an analog thereof, a derivative thereof, or a combination thereof.

5. The method of claim 1, wherein the biologically active material comprises genetic material.

6. The method of claim 1, wherein the coating formulation further comprises a polymeric material and a solvent.

7. The method of claim 1, wherein the tubular wall is grounded, and the conductive core wire and the coating formulation have the same electrical charge.

8. The method of claim 7, wherein the electrical charge of the coating formulation and the electrical charge of the conductive core wire are adjusted so that the charged coating formulation is deposited on the outer surface of the tubular wall and the inner surface remains substantially free of the charged coating formulation.

9. The method of claim 1, wherein the tubular wall is grounded, and the conductive core wire has an electrical charge opposite that of the coating formulation.

10. The method of claim 1, wherein the tubular wall comprises a geometric center, and the conductive core wire is located axially through the center of the tubular wall.

11. The method of claim 1, wherein the potential applied to the conductive core wire is pulsated to cyclically impart a positive electrical charge to the conductive core wire followed by a negative electrical charge.

12. The method of claim 11, wherein a positive electrical charge imparted to the conductive core wire is for a shorter duration than the negative electrical charge imparted to the conductive core wire.

13. The method of claim 11, wherein the coating formulation has a positive electrical charge, and an electrical potential applied to the tubular wall is repeatedly alternated between grounded and positively charged to deposit a desired amount of the coating formulation on each portion of the tubular wall.

14. The method of claim 1, wherein the conductive core wire is kept substantially free of the charged coating formulation.

15. The method of claim 1, wherein the conductive core wire has two ends and one end of the conductive core wire is connected to a first bobbin and the other end is connected to a second bobbin, wherein the conductive core wire is fed from the first bobbin through the tubular wall, and wherein the conductive core wire covered with the coating formulation is removed from the tubular wall by being connected to the second bobbin.

16. The method of claim 1, which further comprises directing the charged coating formulation by providing (a) a first deflector plate having a positive electrical charge and a second deflector plate having a negative electrical charge, which are placed parallel to each other and (b) applying the charged coating formulation between the plates.

17. A method for coating a medical device comprising a tubular wall having an inner surface, an outer surface and openings therein, wherein the method comprises:

(a) grounding or electrically charging the tubular wall;

(b) providing a first core wire comprising a resistor material located axially through the tubular wall;

(c) directing a current through the first core wire;

(d) creating an electrically charged coating formulation comprising a biologically active material; and (e) depositing the coating formulation onto the tubular wall to form a coating on the tubular wall.

18. The method of claim 17, wherein the coating formulation further comprises a polymeric material and a solvent.

19. The method of claim 17, wherein the tubular wall comprises two end sections and wherein a greater amount of coating formulation is applied to one end section than the other.

20. The method of claim 17, which further comprises providing a second care wire comprising a resistor material through the tubular wall wherein the second core wire is parallel to the first core wire; and directing a second current through the second core wire in direction opposite the first current.

21. The method of claim 17, wherein the first core wire is kept substantially free of the coating formulation.

22. The method of claim 17, wherein the first core wire comprising two ends and one end of the first core wire is connected to a first bobbin and the other end is connected to a second bobbin, wherein the first core wire is fed from the first bobbin through the tubular wall, and wherein the first core wire covered with the coating formulation is removed from the tubular wall by being connected to the second bobbin.

23. The method of claim 17, wherein the biologically active material comprises an immunosuppressant, an antiproliferative agent, or a combination thereof.

24. The method of claim 23, wherein the immunosuppressant comprises sirolimus, everolimus, tacrolimus, or a combination thereof.

25. The method of claim 23, wherein the antiproliferative agent comprises paclitaxel, an analog thereof, a derivative thereof, or a combination thereof.

26. The method of claim 23, wherein the coating formulation further comprises a polymeric material and a solvent.

27. The method of claim 17, wherein the biologically active material comprises genetic material.

28. A method for coating at least a portion of a stent, wherein the stent comprises a stent wall having an inner surface, an outer surface and openings therein, wherein the method comprises:

(a) grounding or electrically charging the stent wall;

(b) providing a conductive core wire located axially through the stent;

(c) applying a potential to the conductive core wire to impart an electrical charge to the conductive core wire;

(d) exposing the stent to an electrically charged coating formulation comprising a biologically active material; and (e) depositing the charged coating formulation onto the stent portion to form a coating on the portion.

29. The method of claim 28, wherein the biologically active material comprises an immunosuppressant, an anti-proliferative agent, or a combination thereof.

30. The method of claim 29, wherein the immunosuppressant comprises sirolimus, everolimus, tacrolimus, or a combination thereof.

31. The method of claim 29, wherein the antiproliferative agent comprises paclitaxel, an analog thereof, a derivative thereof, or a combination thereof.

32. The method of claim 28, wherein the biologically active material comprises genetic material.

* * * * *